(12) United States Patent
Hay

(10) Patent No.: US 11,918,068 B2
(45) Date of Patent: Mar. 5, 2024

(54) STERILIZATION SYSTEMS AND METHODS OF USE THEREOF

(71) Applicant: James Scott Hay, Parkland, FL (US)

(72) Inventor: James Scott Hay, Parkland, FL (US)

(*) Notice: Subject to any disclaimer, the term of this patent is extended or adjusted under 35 U.S.C. 154(b) by 373 days.

(21) Appl. No.: 17/321,811

(22) Filed: May 17, 2021

(65) Prior Publication Data

US 2021/0352989 A1 Nov. 18, 2021

Related U.S. Application Data

(60) Provisional application No. 63/026,463, filed on May 18, 2020.

(51) Int. Cl.
| | |
|---|---|
| *A42B 1/0195* | (2021.01) |
| *A42B 3/04* | (2006.01) |
| *A61L 9/20* | (2006.01) |
| *F04D 29/52* | (2006.01) |
| *B60H 3/06* | (2006.01) |

(52) U.S. Cl.
CPC ............... *A42B 3/044* (2013.01); *A61L 9/20* (2013.01); *F04D 29/522* (2013.01); *A61L 2209/12* (2013.01); *A61L 2209/14* (2013.01); *A61L 2209/15* (2013.01)

(58) Field of Classification Search
CPC ....... A42B 3/044; A42B 1/017; A42B 1/0182; A42B 1/244; A61L 9/20; A61L 2209/12; A61L 2209/14; A61L 2209/15; F04D 29/522; F04D 25/084; F04D 29/703; A42C 5/04
See application file for complete search history.

(56) References Cited

U.S. PATENT DOCUMENTS

| | | | | |
|---|---|---|---|---|
| 3,168,748 A | * | 2/1965 | Limberg | A42C 5/04 |
| | | | | 416/63 |
| 3,353,191 A | * | 11/1967 | Dahly | A42C 5/04 |
| | | | | 62/235.1 |
| 3,735,423 A | * | 5/1973 | Droz | A42C 5/04 |
| | | | | D2/866 |
| 3,963,021 A | * | 6/1976 | Bancroft | A62B 18/045 |
| | | | | 128/201.25 |
| 4,893,356 A | * | 1/1990 | Waters | A42B 1/008 |
| | | | | 2/909 |
| 5,048,516 A | * | 9/1991 | Soderberg | A62B 18/003 |
| | | | | 128/205.25 |
| 5,054,480 A | * | 10/1991 | Bare | A41D 13/11 |
| | | | | 128/206.28 |
| 5,267,557 A | * | 12/1993 | Her-Mou | A41D 13/11 |
| | | | | 128/207.13 |
| 5,353,605 A | * | 10/1994 | Naaman | A42B 3/285 |
| | | | | 607/109 |

(Continued)

*Primary Examiner* — Robert H Muromoto, Jr.
(74) *Attorney, Agent, or Firm* — Mark Terry

(57) ABSTRACT

A personal sterilization system, including a base unit defining an air intake, a fan, and a fluid path from the air intake to the fan; at least one UVC light source positioned to illuminate at least a portion of the fluid path with UVC light; a delivery conduit attached to the base unit in fluid communication with the fan; and a dispersion device configured to be worn in proximity to a person's face, the dispersion device defining a fluid inlet attached to the delivery conduit, and at least one fluid outlet configured to disperse pressurized air.

14 Claims, 10 Drawing Sheets

(56) References Cited

U.S. PATENT DOCUMENTS

| | | | | |
|---|---|---|---|---|
| 5,399,319 | A | * | 3/1995 | Schoenberger .... B01D 46/0028 55/385.2 |
| 5,425,620 | A | * | 6/1995 | Stroud ..................... A42C 5/04 403/360 |
| 5,513,632 | A | * | 5/1996 | Nepon ................ A61M 16/009 128/200.28 |
| 5,533,500 | A | * | 7/1996 | Her-Mou .............. A42B 3/288 128/205.12 |
| 5,561,862 | A | * | 10/1996 | Flores, Sr. ............. A42B 3/286 2/422 |
| 5,612,001 | A | * | 3/1997 | Matschke ................. A61L 2/10 422/111 |
| 5,655,374 | A | * | 8/1997 | Santilli .............. A41D 13/1218 2/905 |
| 5,711,033 | A | * | 1/1998 | Green ..................... F04D 17/16 2/424 |
| 5,833,740 | A | * | 11/1998 | Brais ......................... F24F 8/26 96/62 |
| 5,835,840 | A | * | 11/1998 | Goswami ................. A61L 9/20 422/186.3 |
| 6,053,968 | A | * | 4/2000 | Miller ....................... F24F 8/22 96/16 |
| 6,322,614 | B1 | * | 11/2001 | Tillmans ................... A61L 9/16 95/287 |
| 6,372,186 | B1 | * | 4/2002 | Fencl ....................... A61L 9/20 250/435 |
| 6,818,177 | B1 | * | 11/2004 | Turcotte ................. F24F 8/192 250/435 |
| 7,114,194 | B2 | * | 10/2006 | English .................. A42B 3/286 2/171.3 |
| 7,143,451 | B2 | * | 12/2006 | Lundgren ................. A42C 5/04 2/209.13 |
| 7,195,660 | B2 | * | 3/2007 | Little ........................ A47C 7/74 55/467 |
| 7,290,292 | B1 | * | 11/2007 | Nellon ..................... A42C 5/04 2/209.13 |
| 7,410,532 | B2 | * | 8/2008 | Krichtafovitch ........ H01J 49/04 96/77 |
| 7,498,004 | B2 | * | 3/2009 | Saccomanno ........... C02F 1/325 422/186 |
| 9,161,587 | B2 | * | 10/2015 | Green .................... A42B 3/286 |
| 9,162,173 | B1 | * | 10/2015 | Martinez ................ F24F 8/108 |
| 9,486,026 | B1 | * | 11/2016 | Cook, Sr. .............. F04D 25/084 |
| 10,537,754 | B1 | * | 1/2020 | Vukelja ................ A62B 18/003 |
| 11,131,310 | B1 | * | 9/2021 | Emery ..................... H02J 50/10 |
| 2002/0098127 | A1 | * | 7/2002 | Bollini ...................... A61L 9/20 250/436 |
| 2003/0003028 | A1 | * | 1/2003 | Tomaselli ................. A61L 9/20 250/436 |
| 2003/0019505 | A1 | * | 1/2003 | Scheir ................... C07K 14/715 134/1 |
| 2003/0019738 | A1 | * | 1/2003 | Reisfeld .................... A61L 9/20 422/186 |
| 2003/0021720 | A1 | * | 1/2003 | Reisfeld ................... F24F 11/65 422/4 |
| 2003/0165410 | A1 | * | 9/2003 | Taylor .................... A61L 9/015 422/186.04 |
| 2003/0188743 | A1 | * | 10/2003 | Manne ................. A62B 18/003 128/201.22 |
| 2003/0230477 | A1 | * | 12/2003 | Fink ....................... C01B 13/10 204/157.44 |
| 2004/0003810 | A1 | * | 1/2004 | Templeton ............. A62B 17/04 128/201.25 |
| 2004/0055601 | A1 | * | 3/2004 | De Luca ............... A62B 18/003 128/201.25 |
| 2005/0132468 | A1 | * | 6/2005 | Lundgren ................. A42C 5/04 2/171.3 |
| 2005/0175512 | A1 | * | 8/2005 | Yuen ..................... F24F 1/0071 422/121 |
| 2005/0186871 | A1 | * | 8/2005 | Hockaday ............... A61L 2/232 442/76 |
| 2006/0150819 | A1 | * | 7/2006 | Yuen ........................ A61L 9/22 96/224 |
| 2007/0036696 | A1 | * | 2/2007 | McEllen ................. B01D 46/10 422/186.3 |
| 2007/0297951 | A1 | * | 12/2007 | Caramuta ................. A61L 9/20 422/121 |
| 2008/0213129 | A1 | * | 9/2008 | van der Pol ............. F24F 8/22 422/24 |
| 2009/0320316 | A1 | * | 12/2009 | Zakai ..................... A45D 29/00 34/275 |
| 2011/0240883 | A1 | * | 10/2011 | Ullman ..................... A61L 2/10 250/454.11 |
| 2014/0360496 | A1 | * | 12/2014 | Reese ................... A61M 16/1005 128/200.28 |
| 2016/0377085 | A1 | * | 12/2016 | Wang ..................... A42B 1/008 415/177 |
| 2017/0215513 | A1 | * | 8/2017 | Crunk ....................... A42B 1/24 |
| 2018/0014596 | A1 | * | 1/2018 | Washington ......... A42B 1/0182 |
| 2020/0254133 | A1 | * | 8/2020 | Carr ....................... F24F 8/192 |
| 2021/0346554 | A1 | * | 11/2021 | Behzadi ................. A61L 9/046 |

* cited by examiner

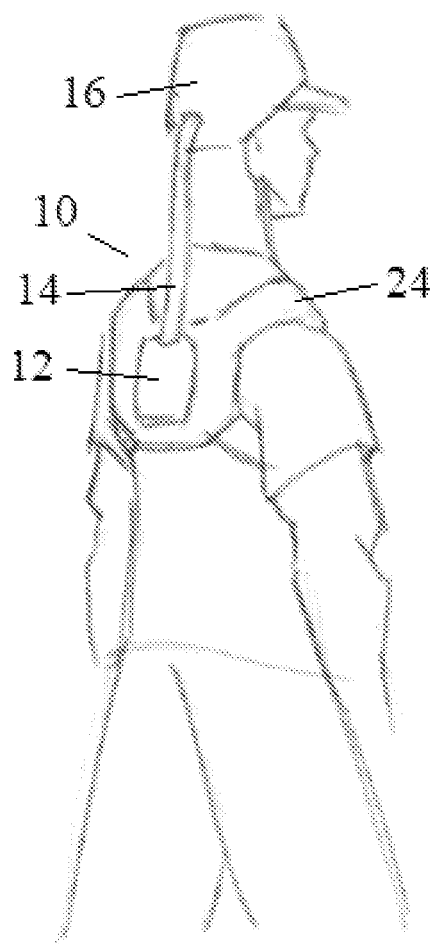 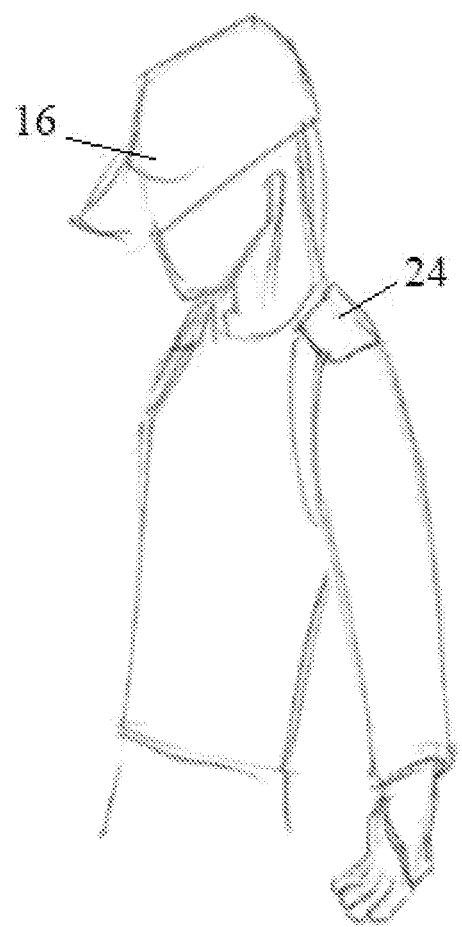
*FIG. 1A*  *FIG. 1B*

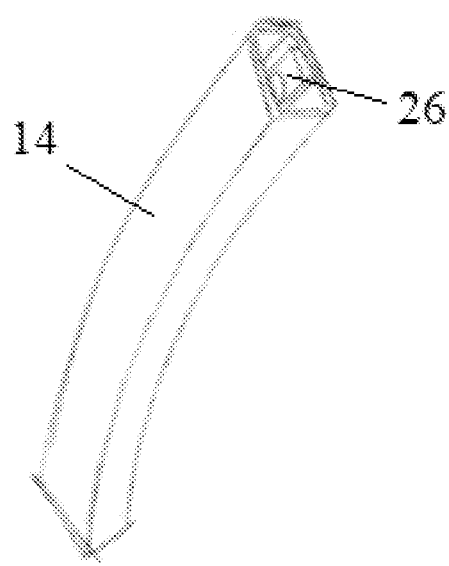
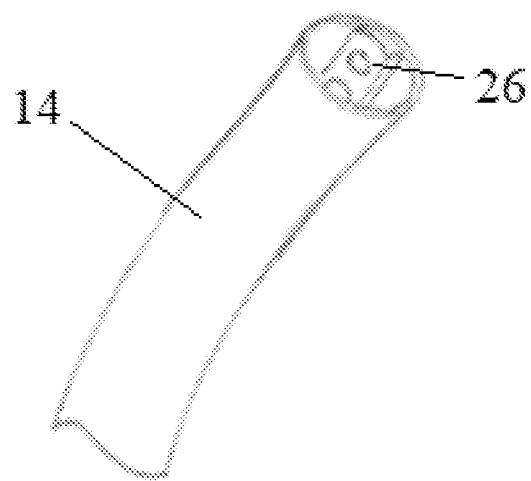
FIG. 5A  FIG. 5B
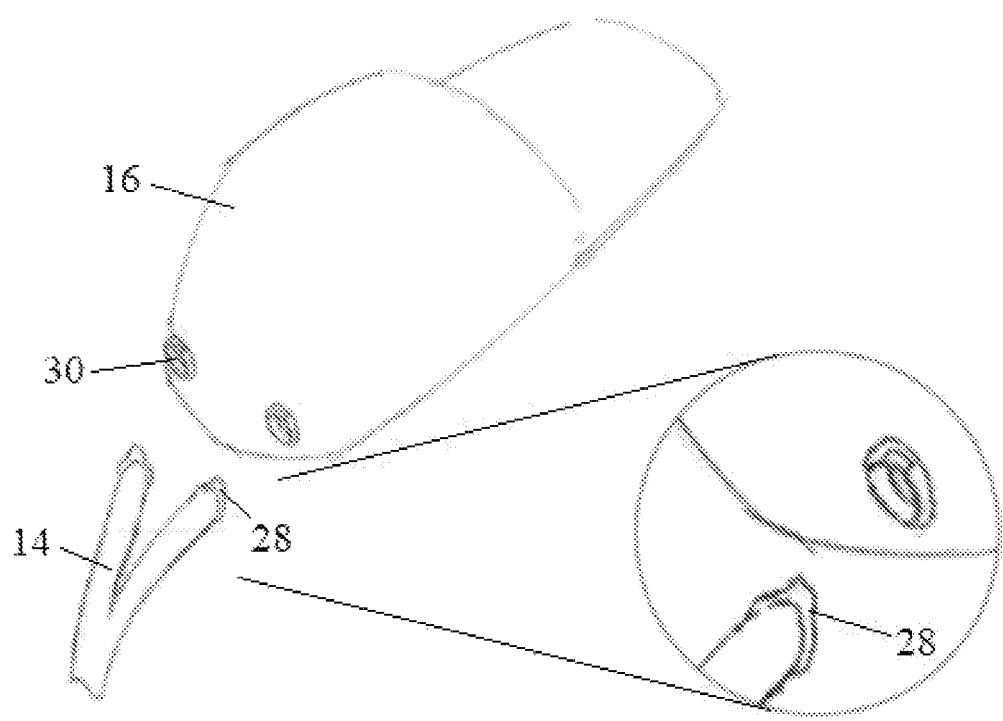
FIG. 5C

US 11,918,068 B2

STERILIZATION SYSTEMS AND METHODS OF USE THEREOF

CROSS-REFERENCE TO RELATED APPLICATION

This application is related to and claims priority to U.S. Provisional Patent Application Ser. No. 63/026,463, filed May 18, 2020, entitled STERILIZATION SYSTEMS AND METHODS OF USE THEREOF, the entirety of which is incorporated herein by reference.

STATEMENT REGARDING FEDERALLY SPONSORED RESEARCH OR DEVELOPMENT n/a

FIELD OF THE INVENTION

The present disclosure relates to systems and methods of use thereof for reducing the transmission and/or reception of pathogens in and about an individual's airways or other entries into the body.

BACKGROUND OF THE INVENTION

During the recent pandemic, large segments of the world's population adorned face masks to prevent the spread of airborne pathogens. However, such masks were not without drawbacks. For example, such masks may not fit the wearer properly to create an effective seal against airborne pathogens, may be hot or otherwise uncomfortable to wear for prolonged periods of time, may become contaminated with growing bacteria over times of prolonged use, and/or may interfere with the wearer's ability to communicate to others.

The present disclosure provides systems and methods of use thereof for reducing the transmission and/or reception of pathogens in and about an individual's airways or other entries into the body to address and overcome the shortcomings of traditional facemasks.

SUMMARY OF THE INVENTION

The present disclosure advantageously provides a personal sterilization system, including: a base unit defining an air intake path leading to a fan; at least one UVC light source positioned to illuminate at least a portion of the air intake path with UVC light; a delivery conduit attached to the base unit in fluid communication with the fan; and a dispersion device configured to be worn in proximity to a person's face, the dispersion device defining a fluid inlet attached to the delivery conduit, and at least one fluid outlet configured to disperse pressurized air. The dispersion device may be a hat. The hat may define a rear section having the fluid inlet, where the hat defines a visor, and where the at least one fluid outlet is located on the visor. The at least one fluid outlet may include a plurality of elongated fluid outlets extending along a perimeter of the visor. The visor may define a cavity therein for the passage of fluid to the at least one fluid outlet. The system may include at least one vane disposed within the cavity to direct the passage of fluid through the cavity. The system may include a fluid bladder extending around at least a portion of the circumference of the hat, where the fluid bladder connects the fluid inlet to the at least one fluid outlet. The dispersion device may include a collar, and two pressurized air outlets extending from the collar. The base unit may include one or more straps configured to attach the base unit to a person's arm. The base unit may include one or more straps configured to attach the base unit to a person's torso. The base unit may be configured to attach to a person's article of clothing. The fan may provide air flow between 10 and 20 CFM. The fan may provide pressurized air output of 30 PSI or less. The system may include at least one UVC light source disposed within the delivery conduit.

A personal sterilization system is provided, including a base unit defining an air intake path leading to a fan; at least one UVC light source positioned to illuminate at least a portion of the air intake path with UVC light; a delivery conduit attached to the base unit in fluid communication with the fan; and a hat, including: a fluid inlet attached to the delivery conduit; a fluid bladder extending along at least a portion of the circumference of the hat and in fluid communication with the fluid inlet; and a visor defining a cavity therein in fluid communication with the fluid bladder and at least one fluid outlet in fluid communication with the cavity. The at least one fluid outlet may include a plurality of elongated fluid outlets extending along a perimeter of the visor. The system may include at least one vane disposed within the cavity of the visor to direct the passage of fluid through the cavity. The system may include at least one UVC light source disposed within the delivery conduit.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIGS. 1A-1B illustrate examples of personal sterilization systems constructed in accordance with the principles of the present disclosure;

FIGS. 5A-5E illustrate examples of delivery conduits and components thereof for personal sterilization systems constructed in accordance with the principles of the present disclosure;

DETAILED DESCRIPTION OF THE INVENTION

The present disclosure provides systems and methods of use thereof for reducing the transmission and/or reception of pathogens in and about an individual's airways or other entries into the body. Examples of such systems may generally include the use of generating positive air pressure in or about an individual's personal space, including about the head or neck areas, and may include the use of sterilizing mechanisms applied to the delivered air as well as directly onto the skin and/or about the individual's airways.

Figure 2:
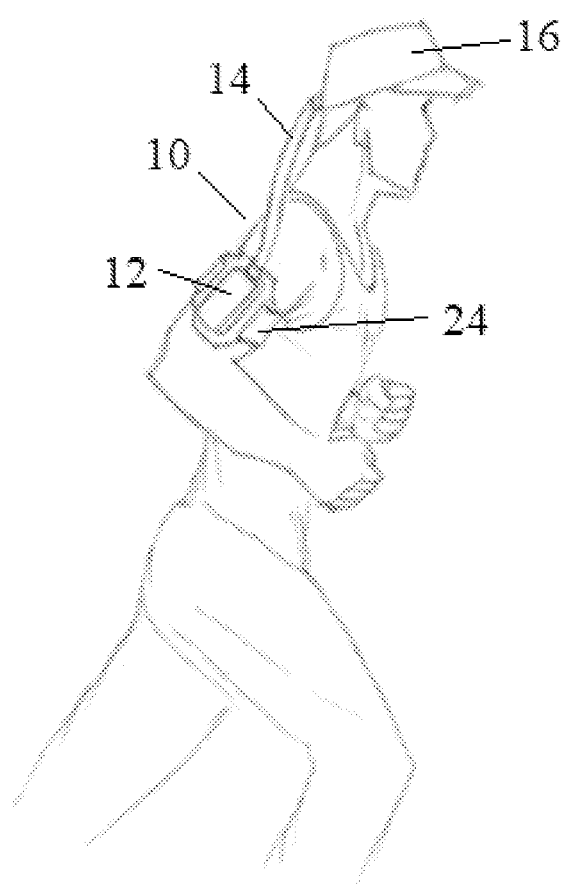
FIG. 2 illustrates another example of a personal sterilization system constructed in accordance with the principles of the present disclosure.
Figure 3:
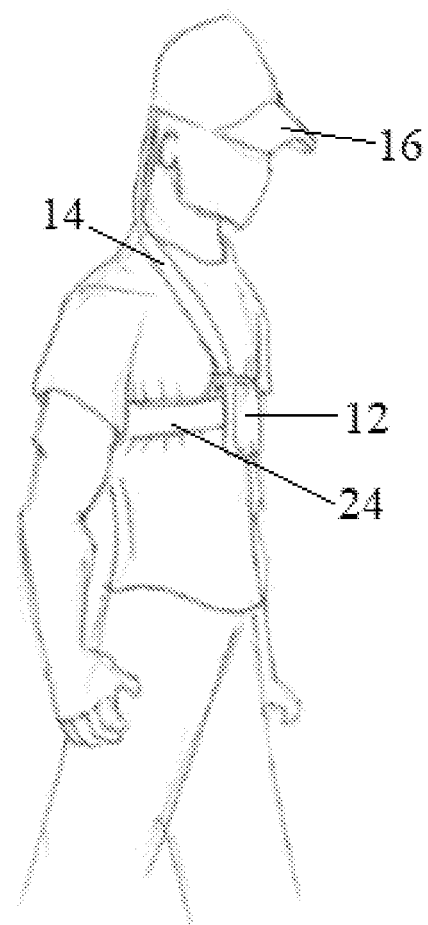
FIG. 3 illustrates another example of a personal sterilization system constructed in accordance with the principles of the present disclosure.
Figure 4A:
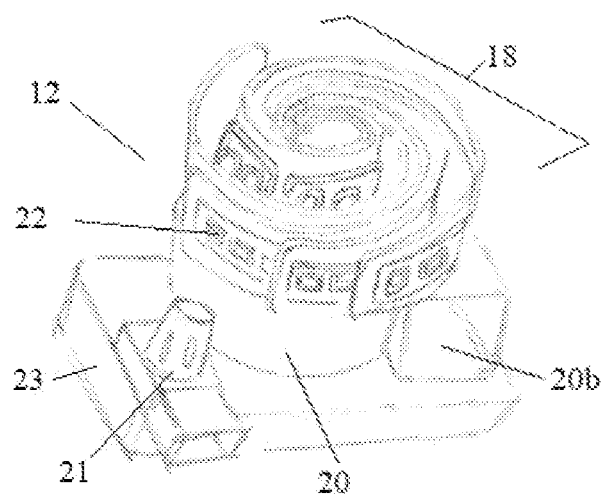
FIGS. 4A-4E illustrate examples of base units and components thereof for personal sterilization systems constructed in accordance with the principles of the present disclosure.
Figure 4B:
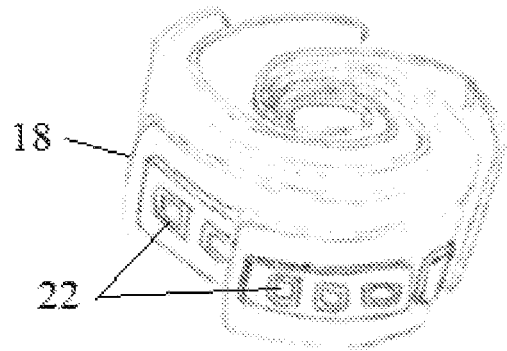
Figure 4C:
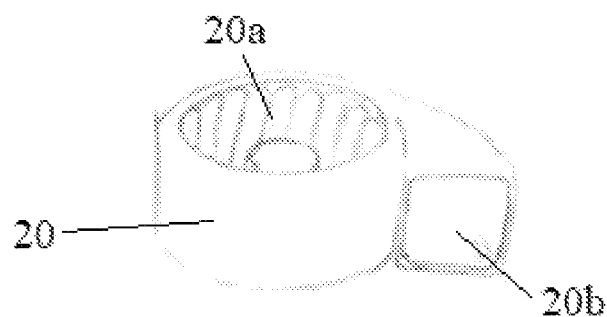
Figure 4D:
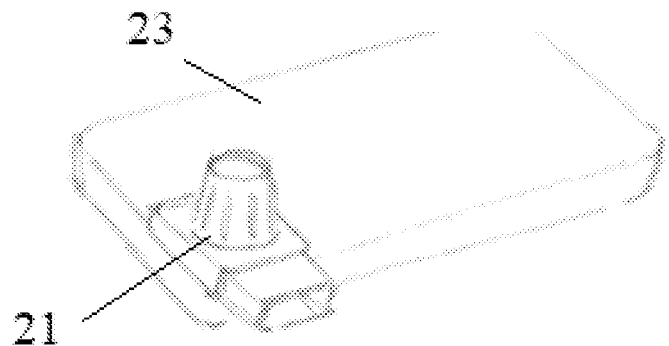
Figure 4E:
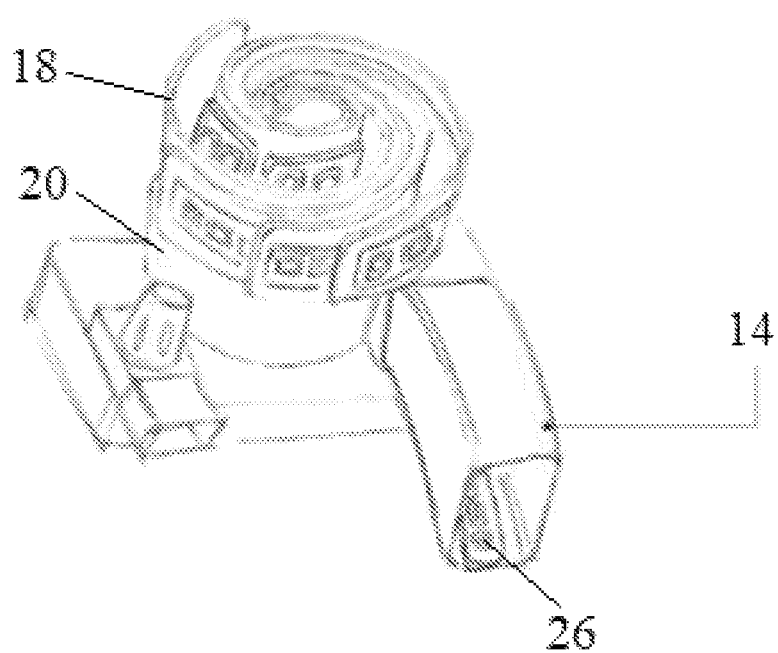

Now turning to FIGS. 1-3, examples of personal sterilization systems constructed in accordance with the principles of the present disclosure are shown, generally designated as '10'. The personal sterilization systems 10 each generally include a base unit 12 providing sterilized airflow, one or more fluid delivery conduits 14, and a fluid dispersion device 16 positionable on or about the head/neck region of an individual.

Now referring to FIGS. 4A-4E, the base unit 12 of the personal sterilization system 10 generates sterilized pressurized airflow. The base unit 12 may include an air intake path 18 leading to a fan 20. The intake path 18 may include one or more structures, baffles, walls, guide vanes, or other components that the air flow moves through or around to reach the fan for subsequent dispersion or delivery to other components of the system 10 as described herein. In the illustrated example, the air intake path 18 includes a plurality of spirally-oriented segments mounted on the fan 20, such that during operation of the fan 20, air is drawn in through the spiral air intake path 18 and into the fan inlet 20a and towards the fan outlet port 20b.

One or more UV/UVC light sources 22 may be positioned in or about the intake path 18 to irradiate or illuminate the air flow passing through the air intake path 18 with UV/UVC light. The light source(s) 22 may include one or more LEDs, bulbs, emitters, or otherwise providing the desired spectrum of light.

Ultraviolet energy is electromagnetic radiation with a wavelength shorter than that of visible light and longer than x-rays, and the International Commission on Illumination (CIE 2003) defines the UV portion of the electromagnetic spectrum as radiation having wavelengths between 100 and 400 nm. The UV spectrum is further divided into UVA (wavelengths of 400 to 315 nm), UVB (315 to 280 nm), UVC (280 to 200 nm), and vacuum UV (VUV; 200 to 100 nm) (IESNA 2000). UVC light, a strong surface disinfection technology, is used worldwide to ensure not only environmental safety but also food safety. UVC light is known to disrupt virus and bacteria replication, and does not appear to penetrate skin or be harmful to eye sight. The UV/UVC light sources 22 may operate between 120 nm and 260 nm to safely kill microbial pathogens in the airflow heading toward the fan 20. Studies have shown that UVC light is effective in killing 99 percent of pathogens exposed to this light when the exposure time is 2 seconds or greater. Accordingly, by providing an air intake path 18 that exposes airflow to UVC illumination for approximately 2 seconds or greater increases the likelihood that potentially harmful pathogens are removed from the airflow. The air intake 18 may include one or more reflective coatings or components to increase the light exposure and/or irradiation of the airflow passing through the intake 18 and towards the fan 20.

The fan 20 may be sized and shaped to provide sufficient airflow to the dispersion device 16 to deflect pathogens and/or other particulates as described further herein. For example, air volume and pressures emanating from the base unit 12 may be approximately 10 to 20 CFM at a maximum of approximately 20 to 30 PSI. The fan 20 may operate in a maximum range of approximately 3,000 RPMs. The base unit 12 may include one or more sound dampening techniques (e.g., silencers, mufflers, etc.) and/or insulating materials (porous liners, rubber isolation pads, etc.) to reduce noise during operation without compromising the airflow output of the base unit 12. The base unit 12 may incorporate active noise cancellation technology to modulate and offset specific noise emissions from the base unit 12.

The base unit 12 may further include one or more buttons, switches, or other controls 21 to operate, and/or may include 'smart' features operable with an application on a smart phone that enables a user to monitor and/or adjust the performance of the base unit at any given time (for example air flow rate, air flow quality, pathogen detection, obstructed airflow alert, power consumption, etc.). Such features can be realized in hardware, software, or a combination of hardware and software and one or more power sources at least partially disposed in a base unit housing or case 23. Any kind of computing system, or other apparatus adapted for carrying out the features and described herein, is suited to perform the functions described herein.

A typical combination of hardware and software could be a specialized or general-purpose computer system having one or more processing elements and a computer program stored on a storage medium that, when loaded and executed, controls the computer system such that it carries out the methods described herein. Features of the present invention can also be embedded in a computer program product that comprises all the features enabling the implementation of the methods described herein, and which, when loaded in a computing system is able to carry out these methods.

The base unit 12 may be wearable or attachable to an individual's belt, pants, purse, or other article of clothing. For example, the base unit may be attached to a person's torso with one or more straps or harnesses 24 as shown in FIGS. 1A-1B and 3. Alternatively, the base unit may be attached to a person's arm or other extremity with one or more straps or harnesses 24 as shown in FIG. 2. In another example, the base unit 12 and/or other components of the system 10 disclosed herein may be incorporated into an article of clothing to reduce the outward appearance of the system 10.

The base unit 12 provides pressurized, sterilized airflow to the delivery conduit 14. The delivery conduit 14 may include one or more flexible and/or malleable conduits to direct sterilized air flow and UVC light to the head/neck/face regions of the individual via the dispersion device 16. The conduits 14 may include, for example, one or more lumens therein for directional airflow, one or more optical conduits or light sources 26 to deliver UVC light within the conduit 14, and/or one or more electrical components and/or lumens to provide electrical communication from the base unit 12 to the dispersion device 16. The flexible and/or malleable characteristics of the conduits 14 enable a person using this device to direct light and/or air flow in an optimal desired direction or position, which may vary depending on an individual's anatomy, position of the base unit 12, and/or engaging in physical activities.

Figure 5D:
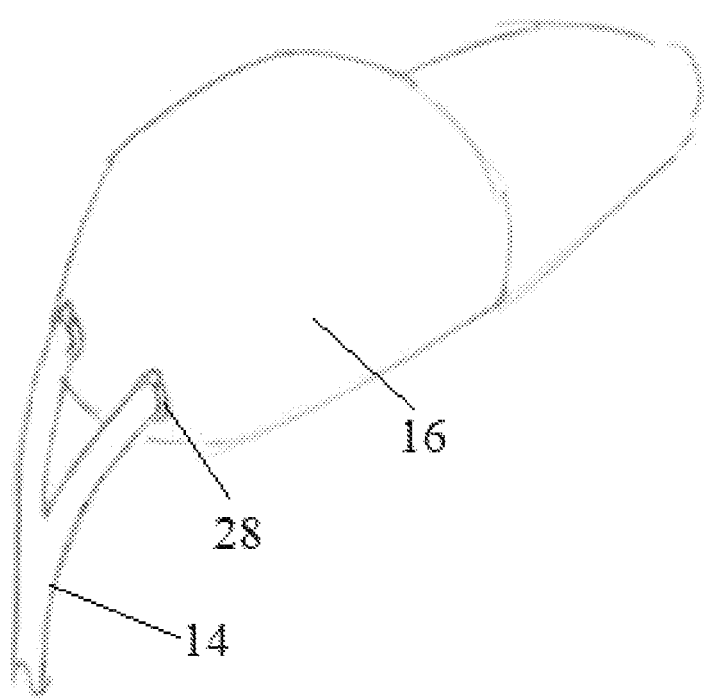
Figure 5E:
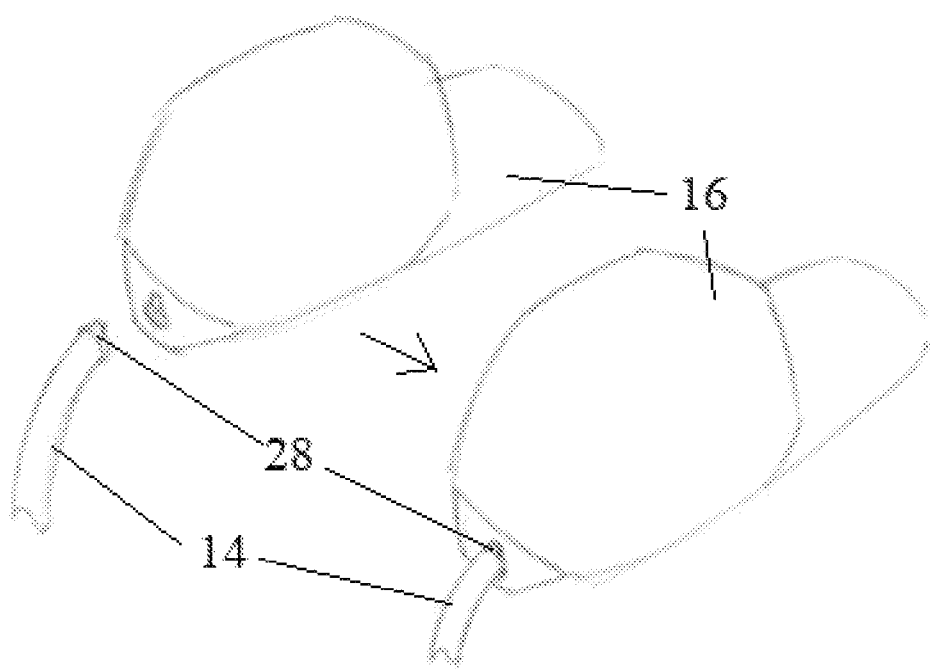

As shown in FIGS. 5A-5B, the delivery conduit 14 may include rounded or rectangular cross-sectional shape profiles. The delivery conduit may also include one or more connectors or adaptors 28 to releasably engage a portion of the dispersion device 16. For example, the delivery conduit may include a self-centering imbedded magnetic attachment component as shown in FIGS. 5C-5E. The delivery conduit 14 may include a "length stretchable" feature employing a helix coiling method or other extendable mechanism for dynamic length adjustment by a user.

Now referring to FIGS. 6A-6F, an example of a wearable dispersion device 16 is shown, generally in the form of a hat. The dispersion device 16 includes a fluid inlet 30 that can couple to and receive pressurized airflow from the delivery conduit 14 and the base unit 12. The fluid inlet 30 may include a fluid flow divider 32 that directs airflow received from the delivery conduit into separate channels or directions within an air/fluid bladder 34 that extends around a portion of the circumference of the hat-styled dispersion device 16.

In the illustrated example, the bladder 34 may be constructed as a low-profile, contoured construct defining a hollow interior that enables laminar airflow from the fluid inlet 30 through the bladder around a cavity or head space of the device 16. The inlet 30 and divider 32 evenly splits the entry air flow into two approximately equal parts and directs each of these two air flows through the bladder 34, which is constructed in a low-profile manner so such airflow channeling is inconspicuous when integrated into wearable garment arrangements like hats and other type clothing. The shape and dimensions of the divider 32 and the inlet 30 may employ an airflow turning method where the radius of the turn to either side of the divider 32 is a multiple equal to 1.5 times the distance of the width of the air pathway. This smooth radius to width design increases uniformity of airflow, greatly reducing turbulence which results in a very low drop in the pressure head of the airflow through the system 10 to efficiently distribute airflow and pressure into a wearable device.

The bladder 34 provides low profile ducting of airflow where pressure head and flow rates are preserved to circumnavigate user anatomy in inconspicuous ways. For example, in the illustrated embodiment, the bladder 34 can replace the inseam of a standard baseball hat where the wearable portion of the hat is not aesthetically impacted in any manner while the airflow characteristics (CFMs and Pressure Head) through the bladder 34 is preserved. The bladder 34 may be used in alternative anatomical areas in shirts and/or sweaters, and/or imbedded into wearable athletic gear to direct pressured air to an airflow dispensing target accessory.

Depending on the wearable application for the dispersion device 16, the bladder 34 may be constructed from rubberized materials and/or hard plastic material combinations. When rubberized materials are employed, the bladder 34 may include internal passage ribbing to ensure adequate spacing within the internal walls of the bladder 34 so pressured air can freely flow to its targeted destination.

The dispersion device 16 may include a visor 36 that defines one or more segments extending from the bladder 34 and defining an interior cavity 38 in fluid communication with the bladder 34 and the fluid inlet 30. In the illustrated example, the visor 36 extends in the form a baseball hat-type visor. Alternative configurations where the visor 36 extends into the brim of a cowboy-type hat, a tennis-styled visor, or other head-mounted article of clothing are contemplated employing the components and methodology disclosed herein. The bladder 34 and/or visor 36 may be enclosed or covered with one or more layers of cloth, fabric, or otherwise to provide a stylized appearance.

Figure 6A:
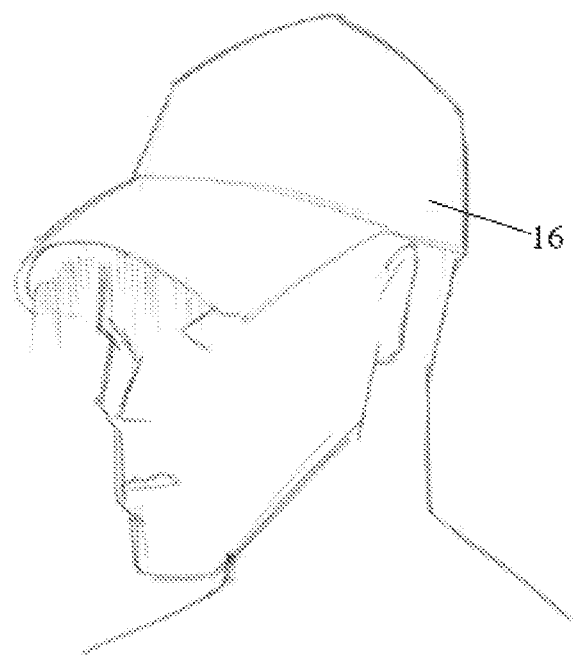
FIGS. 6A-6F illustrate examples of dispersion devices and components thereof for personal sterilization systems constructed in accordance with the principles of the present disclosure.
Figure 6B:
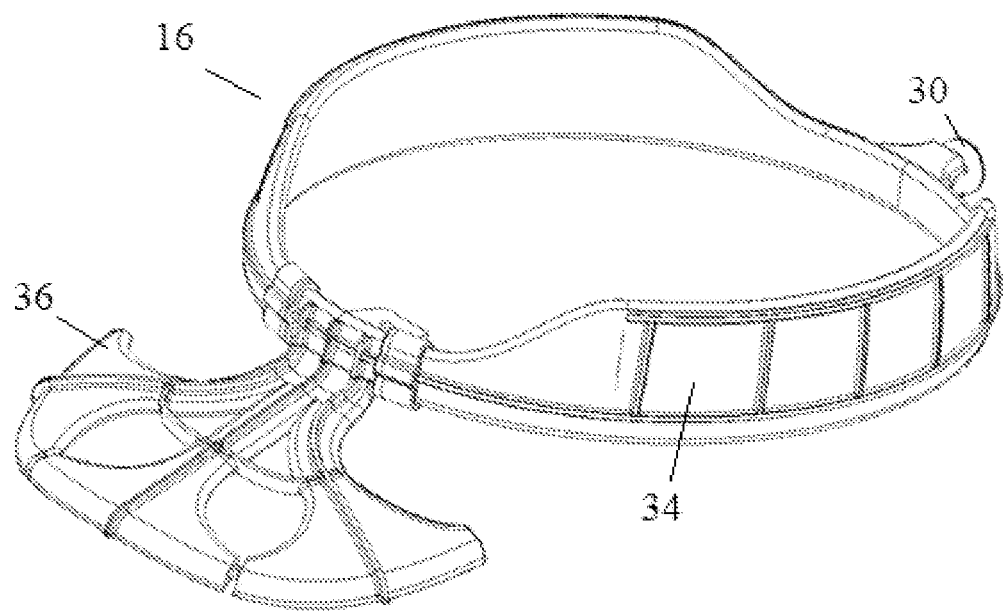
Figure 6C:
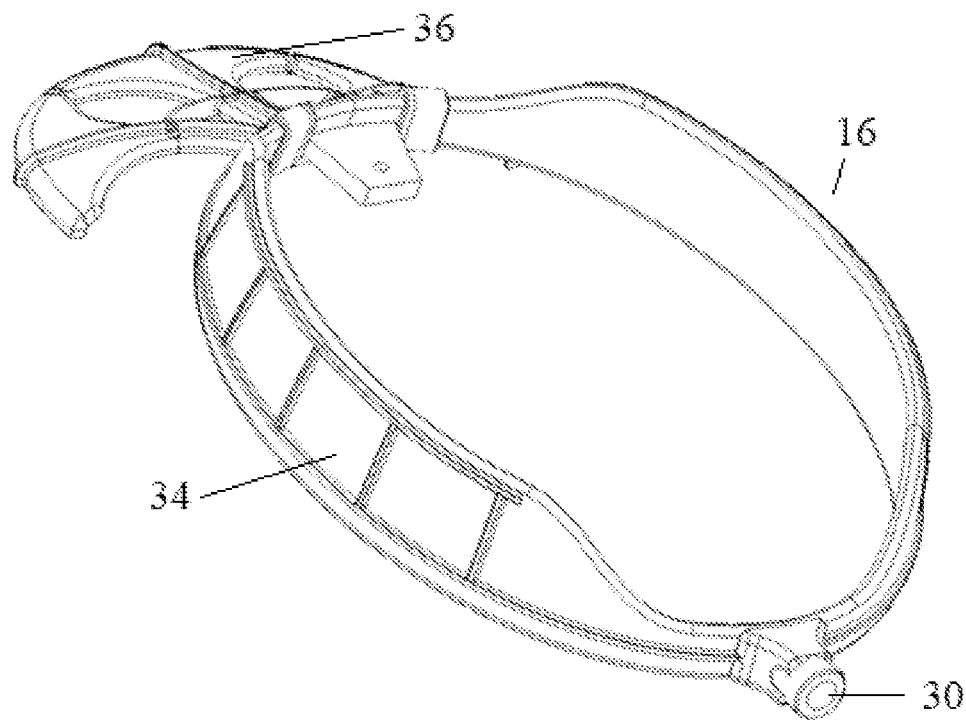
Figure 6D:
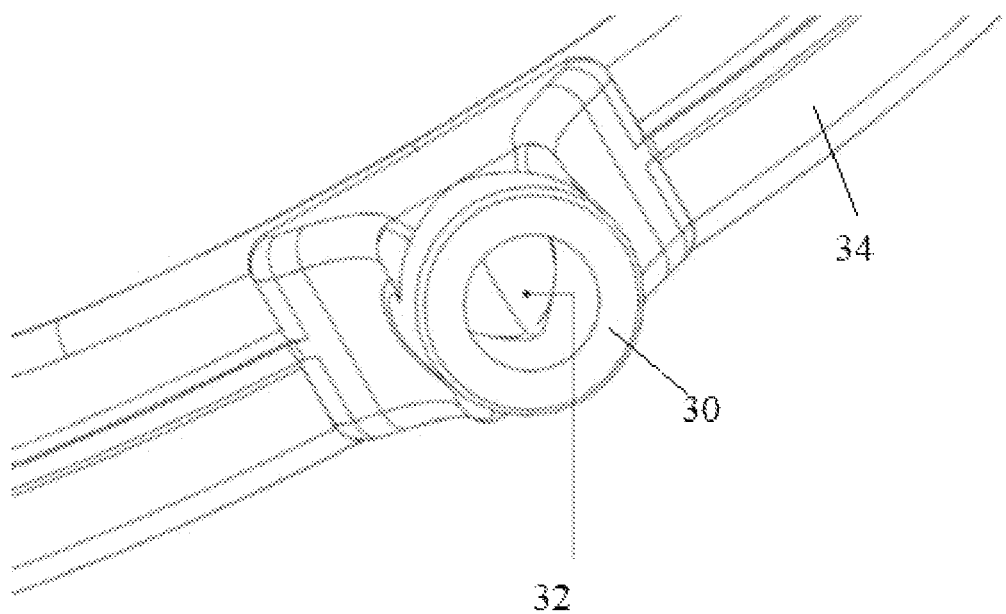
Figure 6E:
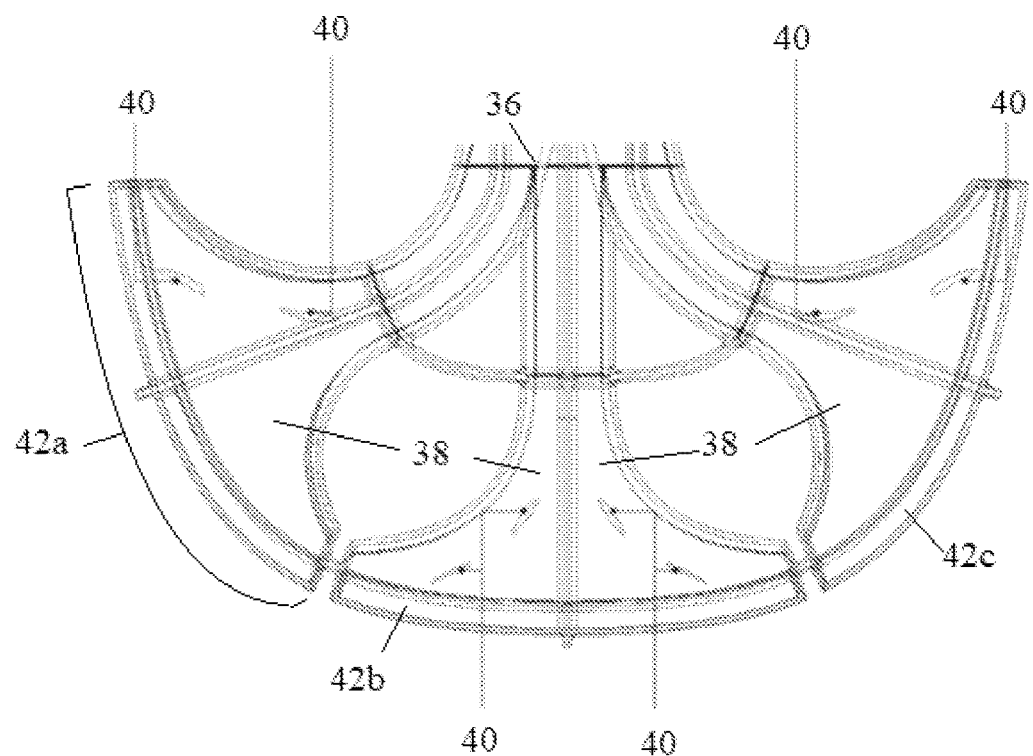
Figure 6F:
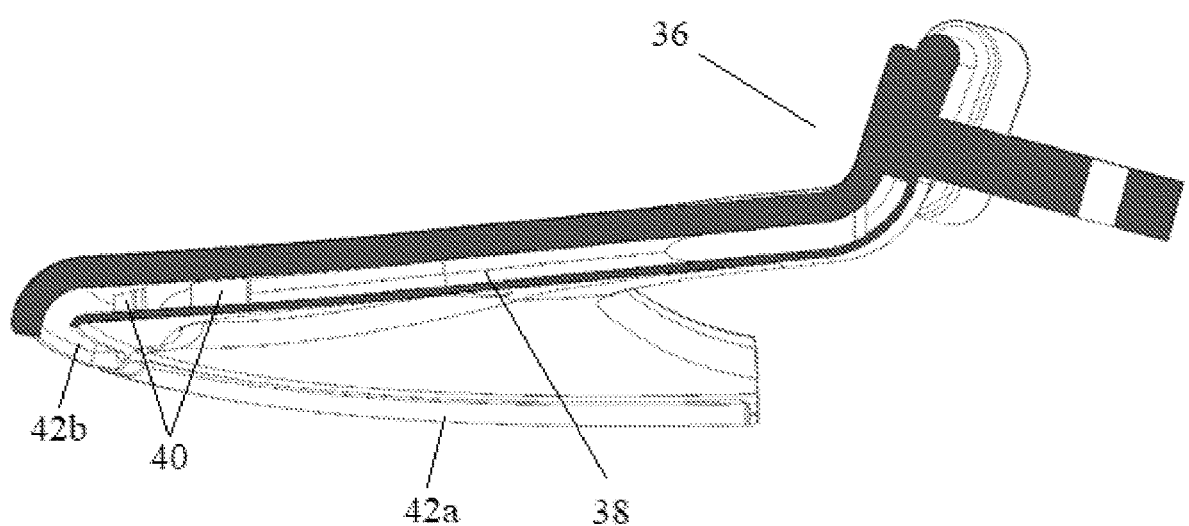

One or more vanes 40 may be disposed within the cavity 38 of the visor 36 to provide laminar airflow through the cavity 38 to one or more air/fluid outlets 42a, 42b, 42c (collectively, "42"), as shown in FIG. 6E and in the cross-sectional view of FIG. 6F. The outlets 42 direct airflow out of the dispersion device 16 and towards the face region of a user to create a positive air pressure region in front of the face to deflect or obstruct incoming pathogens from entries into the body of the wearer, similar to that of an 'air curtain' used when entering a door to a clean room. In the illustrated example, the outlets include a plurality of elongated openings extending along lengths of the outer perimeter of the visor. Additional and/or alternative openings may be provided on other locations in the visor 36 to provide a desired region of positive air pressure and deflection of pathogens from a user's face. Such openings may include adjustable directional nozzles and/or openings with adjustable airflow.

The dispersion device 16 may include one or more filters in the fluid flow path between the inlet 30 and the outlet(s) 42. Such filters may include a HEPA filter, an electrostatic filter, or other air purifying/filtering mechanisms to remove contaminants or particulates from the air flow. The dispersion device 16 may further include one or more buttons, switches, or other external controls to operate, and/or may include 'smart' features operable with an application on a smart phone that enables a user to monitor the performance of the system 10 at any given time (for example air flow rate, air flow quality, pathogen detection, power consumption, etc.).

Figure 7A:
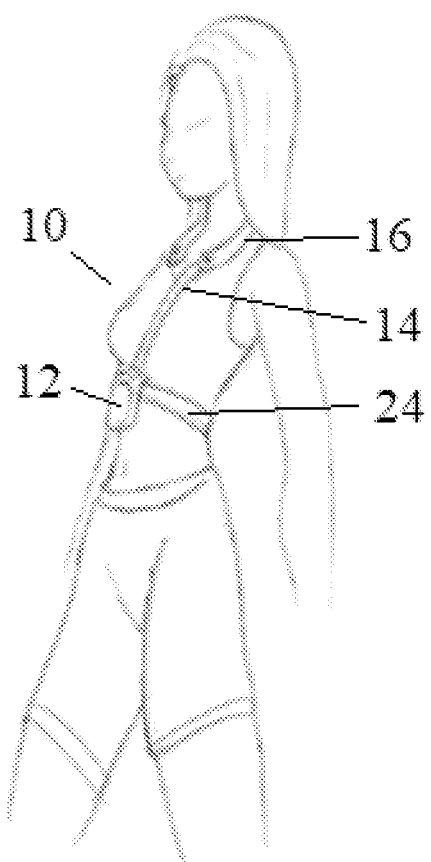
FIGS. 7A-7B illustrate examples of personal sterilization systems constructed in accordance with the principles of the present disclosure.
Figure 7B:
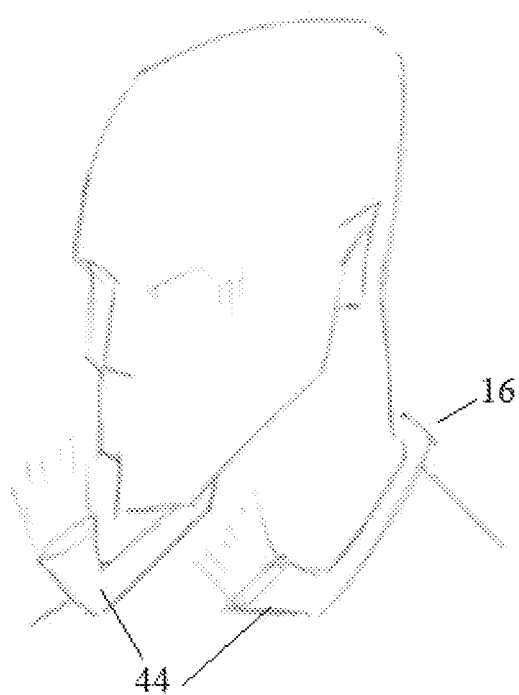

Now referring to FIG. 7A-7B, the dispersion device 16 may be provided in the form of a collar positionable about the neck of an individual. In this example, the dispersion device 16 may receive air flow from the base unit 12 via the delivery conduit 14, and the pressurized, sterilized airflow may flow to the exhaust outlets 42 from one or more tube segments 44. The tube segments may be malleable to allow a user to adjust the position and placement of as desired on the body. In operation, pressurized airflow will exit and extend upwards to create the blocking 'air curtain' to deflect or obstruct incoming pathogens from entry into the face/body openings of the wearer.

Operation of the systems and devices disclose herein aid in creating a safe "air space" environment for the person's face where bacteria and virus would normally reside that have the opportunity to enter into the through their mouth, nose, or eyes. The mouth, nose and eyes are the most likely entry points for a virus and/or bacteria to find its way into a person and the features referenced herein create safe zones to help mitigate viral attacks on the person by protecting the person's face from virus and bacteria.

It will be appreciated by persons skilled in the art that the present disclosure is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the disclosure. A variety of modifications and variations are possible in light of the above teachings without departing from the scope and spirit of the disclosure, which is limited only by the following claims.

What is claimed is:

1. A personal sterilization system for a user, comprising:
a base unit defining an air intake path leading to a fan;
at least one UVC light source positioned to illuminate at least a portion of the air intake path with UVC light;
a delivery conduit attached to the base unit in fluid communication with the fan; and
a hat, including:

a fluid inlet attached to the delivery conduit;

a fluid bladder extending along at least a portion of the circumference of the hat and in fluid communication with the fluid inlet;

a visor defining a cavity therein in fluid communication with the fluid bladder; and at least one fluid outlet within the visor in fluid communication with the cavity, wherein said at least one fluid outlet points air downwards in front of the user's face;

wherein the hat does not intrude upon, or obstruct any portion of, the area in front of the person's face.

2. The system of claim 1, wherein the hat defines a rear section having the fluid inlet.

3. The system of claim 2, wherein the at least one fluid outlet includes a plurality of elongated fluid outlets extending along a perimeter of the visor.

4. The system of claim 2, further comprising at least one vane disposed within the cavity to direct the passage of fluid through the cavity.

5. The system of claim 1, wherein the base unit includes one or more straps configured to attach the base unit to a person's arm.

6. The system of claim 1, wherein the base unit includes one or more straps configured to attach the base unit to a person's torso.

7. The system of claim 1, wherein the base unit is configured to attach to a person's article of clothing.

8. The system of claim 1, wherein the fan provides air flow between 10 and 20 CFM.

9. The system of claim 1, wherein the fan provides pressurized air output of 30 PSI or less.

10. The system of claim 1, further comprising at least one UVC light source disposed within the delivery conduit.

11. A personal sterilization system for a user, comprising:

a base unit defining an air intake path leading to a fan;

at least one UVC light source positioned to illuminate at least a portion of the air intake path with UVC light;

a delivery conduit attached to the base unit in fluid communication with the fan;

and a hat, including:

a fluid inlet attached to the delivery conduit;

an oval crown structure configured for sitting on the user's head;

a fluid bladder extending along at least a portion of the circumference of the crown structure and in fluid communication with the fluid inlet;

a visor defining a cavity therein in fluid communication with the fluid bladder the visor connected to the crown structure;

and at least one fluid outlet within the visor in fluid communication with the cavity, wherein said at least one fluid outlet is located at an outer perimeter of the visor, and wherein said at least one fluid outlet points air downwards in front of the user's face;

wherein the hat does not intrude upon, or obstruct any portion of, the area in front of the person's face.

12. The system of claim 11, wherein the at least one fluid outlet includes a plurality of elongated fluid outlets extending along a perimeter of the visor.

13. The system of claim 11, further comprising at least one vane disposed within the cavity of the visor to direct the passage of fluid through the cavity.

14. The system of claim 11, further comprising at least one UVC light source disposed within the delivery conduit.

* * * * *